(12) United States Patent
Nauche et al.

(10) Patent No.: US 10,492,677 B2
(45) Date of Patent: Dec. 3, 2019

(54) OPTOMETRY APPARATUS, ASSEMBLY AND SYSTEM COMPRISING SUCH AN APPARATUS

(71) Applicant: ESSILOR INTERNATIONAL, Charenton-le-Pont (FR)

(72) Inventors: Michel Nauche, Charenton-le-Pont (FR); Stéphane Boutinon, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 0 days.

(21) Appl. No.: 15/757,600

(22) PCT Filed: Aug. 31, 2016

(86) PCT No.: PCT/FR2016/052160
§ 371 (c)(1),
(2) Date: Mar. 5, 2018

(87) PCT Pub. No.: WO2017/037386
PCT Pub. Date: Mar. 9, 2017

(65) Prior Publication Data
US 2018/0242837 A1 Aug. 30, 2018

(30) Foreign Application Priority Data
Sep. 3, 2015 (FR) ..................................... 15 58191

(51) Int. Cl.
*A61B 3/04* (2006.01)
*A61B 3/103* (2006.01)
(Continued)

(52) U.S. Cl.
CPC ................ *A61B 3/04* (2013.01); *A61B 3/005* (2013.01); *A61B 3/0025* (2013.01); *A61B 3/103* (2013.01); *A61B 3/14* (2013.01)

(58) Field of Classification Search
CPC ......... A61B 3/04; A61B 3/113; A61B 3/0285; A61B 3/02; G02C 13/003
(Continued)

(56) References Cited

U.S. PATENT DOCUMENTS

2004/0032568 A1 2/2004 Fukuma et al.
2005/0264760 A1* 12/2005 Ikezawa ................. A61B 3/032
351/239

(Continued)

FOREIGN PATENT DOCUMENTS

CN 103365065 10/2013
EP 2 034 338 A1 3/2009
(Continued)

OTHER PUBLICATIONS

International Search Report, dated Nov. 24, 2016, from corresponding PCT/FR2016/052160 application.
(Continued)

*Primary Examiner* — Mohammed A Hasan
(74) *Attorney, Agent, or Firm* — Young & Thompson (57) ABSTRACT

Disclosed is an optometry apparatus including: a base designed to receive corrective eyeglasses; at least one transmission element designed to cooperate with a member for regulating an optical correction characteristic of the eyeglasses; and at least one drive motor for driving the transmission element. Also disclosed is an assembly and to an associated system.

14 Claims, 3 Drawing Sheets

(51) Int. Cl.
*A61B 3/00* (2006.01)
*A61B 3/14* (2006.01)

(58) Field of Classification Search
USPC .......................................................... 351/229
See application file for complete search history.

(56) References Cited

U.S. PATENT DOCUMENTS

| | | |
|---|---|---|
| 2013/0258056 A1 | 10/2013 | Jang et al. |
| 2015/0190047 A1* | 7/2015 | Sugiura .................. A61B 3/036 351/233 |
| 2016/0331226 A1 | 11/2016 | Nauche et al. |

FOREIGN PATENT DOCUMENTS

| | | |
|---|---|---|
| EP | 2 645 165 A2 | 10/2013 |
| JP | 2001 340296 A | 12/2001 |
| WO | 92/19149 A1 | 11/1992 |
| WO | 2007/026368 | 3/2007 |
| WO | 2015/107303 A1 | 7/2015 |

OTHER PUBLICATIONS

Chinese Office Action for Application No. 201680051089.1, dated Mar. 5, 2019, with English translation provided.

* cited by examiner

OPTOMETRY APPARATUS, ASSEMBLY AND SYSTEM COMPRISING SUCH AN APPARATUS

TECHNICAL FIELD OF THE INVENTION

The present invention relates to the field of optometry.

It relates more particularly to an optometry apparatus, as well as to an assembly and a system comprising such an apparatus.

TECHNOLOGICAL BACKGROUND

In the context of the measurement of the visual acuity of a patient, it has already been proposed to simulate the visual compensation to be provided, for example by means of trial spectacles or a refractor such as a refraction head.

In the refraction head, trial lenses are placed on a plurality of discs that are rotated manually or using a motorized mechanism. However, it will be understood that such an object has a substantial bulk and weight related to the number of lenses placed on each disk.

Trial spectacles are less bulky. Provision is indeed made for them to successively receive trial lenses having different corrections, until the correction which is appropriate for the patient is found.

This solution is however rather impractical, particularly because it requires separate storage of the trial lenses in dedicated boxes. It furthermore involves lens changes, resulting in undesired and non-continuous transitions in corrective power.

SUBJECT OF THE INVENTION

In this context, the present invention proposes an optometry apparatus comprising a holder designed to receive visual compensation spectacles, characterized in that it comprises at least one transmission element designed to cooperate with a member for adjusting an optical correction characteristic of said spectacles and at least one motor for driving the transmission element.

The optometry apparatus thus comprises the motor which makes it possible to adjust, by acting on the adjusting member, the correction obtained by virtue of the spectacles. The spectacles are thereby made correspondingly lighter and are thus very suitable for being worn for a trial of the chosen correction.

According to other optional and therefore nonlimiting characteristics:

- a communication module is designed to receive a setpoint originating from an exterior electronic device;
- a control module is designed to control the driving motor as a function of the setpoint received;
- the optometry apparatus comprises a display and an imager which are disposed on either side of a region of reception of the visual compensation spectacles;
- the optometry apparatus comprises a module for analysis of an image of the display, generated by the imager, and a module for control of the driving motor as a function of data generated by the analysis module.

The invention also proposes an assembly comprising an optometry apparatus and visual compensation spectacles, the optometry apparatus comprising a holder for receiving said spectacles, characterized in that the optometry apparatus comprises at least one transmission element designed to cooperate with a member for adjusting an optical correction characteristic of said spectacles and at least one motor for driving the transmission element.

According to other optional and therefore nonlimiting characteristics:

- the visual compensation spectacles comprise at least one lens having an optical axis;
- the visual compensation spectacles are designed to modify, in case of movement of the adjusting member, a spherical power along the optical axis, generated by said lens;
- the visual compensation spectacles are designed to modify, in case of movement of the adjusting member, a cylindrical correction along the optical axis, generated by said lens;
- the visual compensation spectacles are designed to modify, in case of movement of the adjusting member, a power of said cylindrical correction;
- the visual compensation spectacles are designed to modify, in case of movement of the adjusting member, an axis of said cylindrical correction.

The invention finally proposes a system comprising an optometry apparatus such as mentioned hereinabove and said exterior electronic device, characterized in that said exterior electronic device is another optometry device, for example an auto-refractometer or a refractor.

Provision may be made for said exterior electronic device to determine said setpoint as a function of an ametropia or astigmatism measurement.

DETAILED DESCRIPTION OF AN EXEMPLARY EMBODIMENT

The description which follows with reference to the appended drawings, which are given by way of nonlimiting examples, will make it easy to understand what the invention consists of and how it can be achieved.

Figure 1:
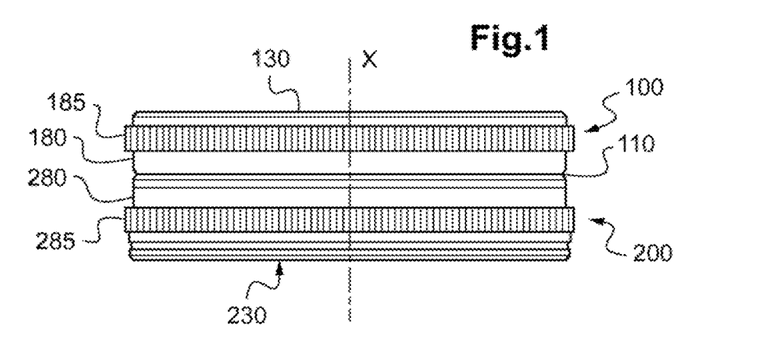
FIG. 1 represents an optical assembly comprising a lens of variable cylindrical power and a lens of variable spherical power.
Figure 2:
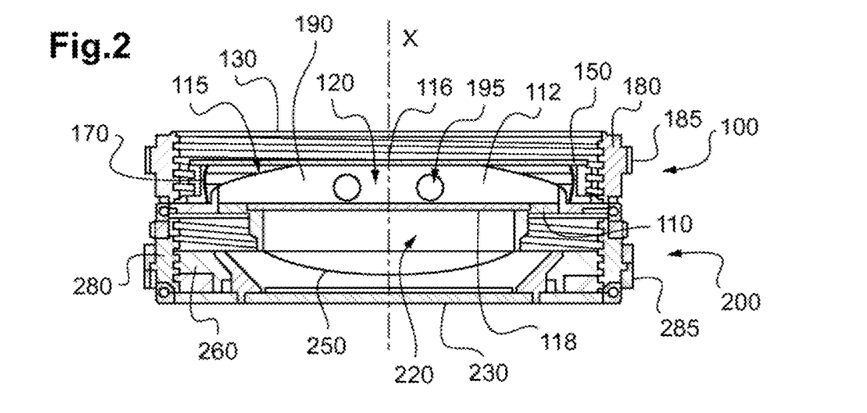
FIG. 2 represents a sectional view of the optical assembly of FIG. 1.
Figure 3:
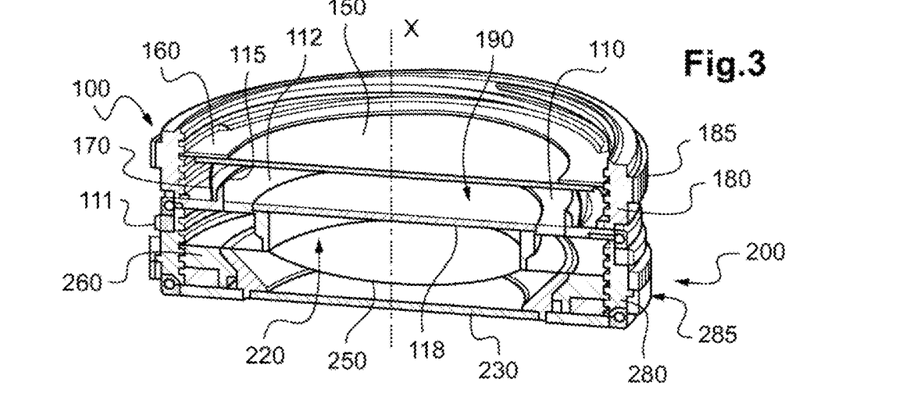
FIG. 3 represents a perspective cut-away of the optical assembly of FIG. 1.

In the appended drawings:

FIGS. 1 to 3 show an optical assembly comprising a first lens 100 and a second lens 200.

The first lens 100 and the second lens 200 are here respectively located on either side of one and the same stand (or body) 110. A (transparent) undeformable separating platen 118, which is mounted on the common stand 110, defines the liquid-filled chambers of the first lens 100 and the second lens 200, as explained below, and thus allows the two lenses 100, 200 to operate independently.

As a variant, either one of the two lenses 100, 200 could be separate. Below, each lens 100, 200 is described separately.

As explained below, the first lens 100 is designed to generate, along an optical axis X of the first lens, a variable cylindrical optical power.

The second lens 200 is for its part designed to generate, along its optical axis, which is identical to the optical axis X of the first lens 100, a variable spherical optical power.

The first lens 100 comprises the stand (or body) 110 and a flexible transparent plate 150.

The stand 110 has a central opening 120 that is closed at one end by a first (transparent) closing plate 130 and at the other end by the separating platen 118; the flexible transparent plate 150 is located in the central opening 120, between the first closing plate 130 and the separating platen 118.

Two walls integrated into the stand 110 allow the flexible plate 150 to be guided in such a way as to prevent any rotation of the flexible plate 150 around the optical axis X.

The stand 110 has a ridge 115 that lies on the periphery of the central opening 120 and that is inscribed in a cylindrical surface the axis of which is perpendicular and secant to the optical axis X.

The stand 110 for example comprises to this end a wall 112 that encircles the central opening 120 and the free end edge of which defines the aforementioned ridge 115.

The function of the ridge 115 is to create a stop that serves as a starting point for the curvature of the flexible plate 150 (by bending), as explained below. The cylindrical shape of the ridge 150 (i.e. the cylindrical surface in which the ridge 115 is inscribed) thus has a radius smaller than the radius corresponding to the maximum desired cylindrical power— typically about 40 mm or less.

The first lens 100 also comprises a first control part 160 that is securely fastened to the flexible plate 150.

The first control part 160 here takes the form of an annular control platen encircling the central opening 120 and including, level with each of two zones that are 180° opposite, an external thread.

The first control part 160 is mounted in the stand 110 so as to be guided in translation along the optical axis X.

The first lens 100 also comprises a first elastic membrane 170 of cylindrical shape and connecting the stand 110 and the first control part 160.

The flexible plate 150, the first control part 160, the first elastic membrane 170, the intermediate platen 118 and the stand 110 form a chamber filled with a liquid 190. Here, this liquid 190 is identical to that used in document U.S. Pat. No. 8,000,022, namely silicone oil (for example of the Rhodrosil oil 47 type).

The stand 110 includes apertures 195 for passage of fluid in the aforementioned wall 112 in order to facilitate the passage of the liquid between the various portions of the chamber.

The first elastic membrane 170 is designed to deform (by stretching in particular) in order to compensate for variations in the volume of the chamber filled with the liquid 190 caused by the bending of the flexible plate 150, as described below. As is clearly shown in FIGS. 2 and 3, the first elastic membrane 170 is located on the periphery of the stand 110 and therefore plays no optical role.

The cylindrical first lens 100 lastly comprises a first control ring 180, which may be moved only rotationally through a given angle around the optical axis X. The first control ring 180 includes an internal thread (here of square cross section) centered on the optical axis X and that engages with the external thread of the first control part 160.

The first control ring 180 also has a plurality of teeth 185 right round its periphery so as to form a toothed wheel and to thus be able to be driven to rotate by a first driving system (not shown), for example a motor the output axle of which comprises a worm screw that interacts with the teeth 185 of the first control ring 180.

Provision may moreover be made to limit the travel of the first control ring 180, for example by means of a hard stop formed between the stand 110 and the first control ring 180.

The motions that allow the flexible plate 150 to be bent and thus a variable cylindrical optical power to be obtained will now be described.

Below, the first control part 160 is considered to be in its highest position (considering the orientation in FIG. 2) i.e. the closest to the first closing plate 130, as shown in FIGS. 2 and 3. As may be seen in these figures, in this position of the first control part 160, the flexible plate 150 does not make contact with the ridge 115.

When the first control ring 180 is rotated (for example by means of the aforementioned first driving system), the first control part 160 begins to be translated (downward in FIG. 2) by way of the bolt/nut system, through a few degrees, until the flexible plate 150 makes contact with the cylindrical ridge 115 that is securely fastened to the stand 110 (this contact occurring first at the top 116 of the ridge 115 in FIG. 2, i.e. in the plane containing the optical axis X and the axis of the cylindrical surface containing the ridge 115).

By continuing the rotation of the first control ring 180, the assembly formed from the first control part 160 and the flexible plate 150 continues its translation (downward in FIG. 2, i.e. away from the first closing plate 130) so that the flexible plate 150 begins to gradually bend, with a (bend) radius value directly related to the angle of rotation of the first control ring 180.

By virtue of the ridge of cylindrical shape, the flexible plate 150 will preferentially deform to a cylindrical shape, this allowing the sought-after cylindrical correction to be obtained, which has a variable power depending on the value of the aforementioned bending radius.

Moreover, due to the fact that the deformation of the flexible plate is initiated by the ridge 150 inscribed in a cylindrical surface, the axis of this cylindrical correction corresponds to the axis of this cylindrical surface (i.e. to an axis that is fixed with respect to the stand 110 and perpendicular to the optical axis X).

It will be noted that the flexible plate 150 in general also undergoes a second deformation of greater or lesser magnitude depending in particular on its anisotropy, its bending stiffness and on the pressure increase associated with the deformation of the first elastic membrane 170. Thus, the flexible plate 150 in general does not have a purely cylindrical shape, but a toric shape.

The additional spherical component will then possibly optionally be compensated for by other optical means, here via action on the second lens 200 described below.

During the deformation of the flexible plate 150, the volume within the chamber filled with the liquid 190 remains constant. Specifically, the pressure increase generated by the deformation of the flexible plate 150 causes the first elastic membrane 170 to deform so as to absorb the transfer of liquid 190 originating from the useful zone.

It will moreover be noted that this slight pressure (applied by the flexible plate 150) allows the motion to be made reversible, while ensuring play is removed from the bolt/nut system.

In summary, by driving the first control ring 180 to rotate by means of the first driving system, the cylindrical power of the first lens 100 is made to vary as explained above (the axis of the cylindrical correction in contrast being fixed with respect to the stand 110 as explained above).

The second lens 200 comprises a support having a central opening 220, a second elastic membrane 250 received in the central opening 220, a second control part 260 that is securely fastened to the second elastic membrane 250, and a second control ring 280.

The support of the second lens 200 is here securely fastened to the stand 110 of the first lens 110 and for example forms a single part therewith.

The second control part 260 is mounted so as to be guided translationally in the support, here by means of three guiding columns.

The second control ring 280 may be moved only rotationally about the optical axis X and allows, during its rotational motions, the second control part 260 to be moved translationally along the optical axis X by means of a bolt/nut system (for example formed by an internal thread of the second control ring 280 that interacts with an external thread of the second control part 260).

The second elastic membrane 250, the second control part 260, the separating platen 118 and the support (here the common stand 110) form a liquid-filled chamber such that the translational motion of the second control part 260 causes an elastic deformation (with stretching) of the second elastic membrane 250, which thus adopts an essentially spherical shape, with a radius of curvature dependent on the position of the second control part 260.

Thus the sought-after variable spherical power is obtained.

The second control ring 280 right round its periphery has a plurality of teeth 285 so as to form a toothed wheel and to thus be able to be driven to rotate by a second driving system (not shown), for example a motor the output axle of which comprises a worm screw that interacts with the teeth 285 of the second control ring 280.

Thus, by driving the second control ring 280 to rotate by means of the second driving system, the spherical power of the second lens 200 is made to vary as explained above.

The entirety of the movement is without structural play. By virtue of this feature, it is possible to establish a control law for the movement that is continuous. Specifically, in the contrary case, since the direction of the forces exerted on the movement invert when the membrane passes from a convex shape to a concave shape, any structural play would risk throwing off the control law or complicating the definition of this control law.

As described hereinabove, it is possible to vary the cylindrical power and the spherical power of the correction obtained by the optical assembly formed of the first lens 100 and of the second lens 200 by driving the first control ring 180 and the second control ring 280 respectively in rotation.

In order to make the cylinder axis of the cylindrical correction obtained with the first lens 100 vary, the aforementioned optical assembly may be mounted so as to be able to rotate about the optical axis X with respect to a fixed frame of reference (in particular with respect to the eye of the patient in front of whom the optical assembly is placed in the context of an examination of subjective refraction).

Accordingly, provision is then for example made for an assembly of teeth 111 provided on the external wall of the stand 110, on the periphery of the optical assembly.

Provision may be made for the rotation of the stand 110 with respect to the fixed frame of reference to drive a rotational movement of the stand on the one hand with respect to the first control ring 180 and on the other hand with respect to the second control ring 280 (these two control rings 180, 280 being immobile in the fixed frame of reference in the absence of driving by the first and second driving systems).

In this case (when it is desired to vary only the cylinder axis of the cylindrical correction) provision is made to drive the control rings 180, 280 in rotation (simultaneously or not with the rotation of the stand 110) in such a way as to preserve the relative position of the stand 110, of the first control ring 180 and of the second control ring 280 so as to preserve the desired values of cylindrical power and of spherical power.

Figure 4:
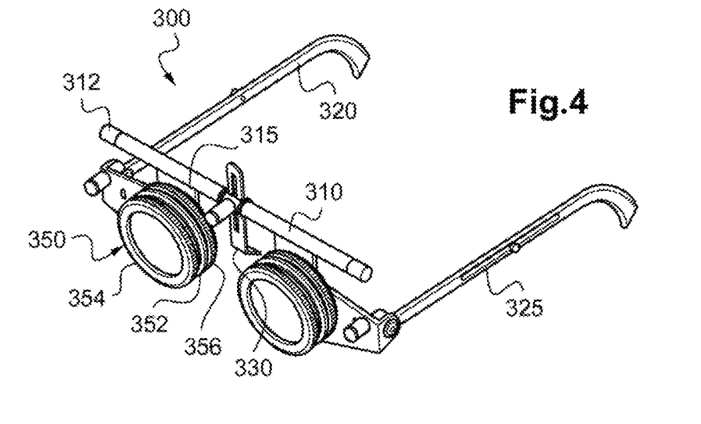
FIG. 4 represents visual compensation spectacles comprising two such optical assemblies.

FIG. 4 represents visual compensation spectacles 300 comprising two optical assemblies 350 such as described hereinabove with reference to FIGS. 1 to 3, mounted on a frame.

The frame comprises a crosspiece 310 which carries two support elements 315 each intended to accommodate an optical assembly 350.

The position of each support element 315 on the crosspiece 310 is adjustable in translation along the axis of the crosspiece 310, here by acting on a pinion 312 disposed at a corresponding end of the crosspiece 310, so as to be able to set the position of the optical assembly 350 concerned to the semi-interpupillary distance of the wearer of the visual compensation spectacles 300.

Each support element 315 carries an optical assembly 350, while allowing this optical assembly 350 a possibility of rotation about its axis when it is driven in rotation by an exterior driving system, as described hereinafter, by means of the toothed wheel 352 formed around its stand as indicated above (see in particular the teeth 111 in FIG. 3).

Each optical assembly 350 is moreover mounted on the corresponding support element 315 in such a way that the first control ring 354 (corresponding to the first control ring 180 in FIGS. 1 to 3) and the second control ring 356 (corresponding to the second control ring 280 in FIGS. 1 to 3) are left accessible (in a region at least).

Otherwise, for each assembly 350, provision may optionally be made for a cowling (not represented) which covers the control rings 354, 356 (so as make it impossible for the latter to be manipulated by a user) except at the places where the control rings 354, 356 cooperate with the transmission elements 425, 435 as explained further on.

Each support element 315 moreover carries a temple 320 of the frame of the visual compensation spectacles 300, with a possibility of orientation of the temple 320 concerned with respect to the support element 315 so as to be able to set the orientation of the temple 320 to the pantoscopic angle of the wearer.

Each temple 320 moreover comprises a mechanism 325 for adjusting the length of the temple concerned.

The crosspiece 310 moreover carries a nasal support 330. The position (height-wise) of the nasal support 330 is adjustable so as to match the morphology of the wearer.

Figure 5:
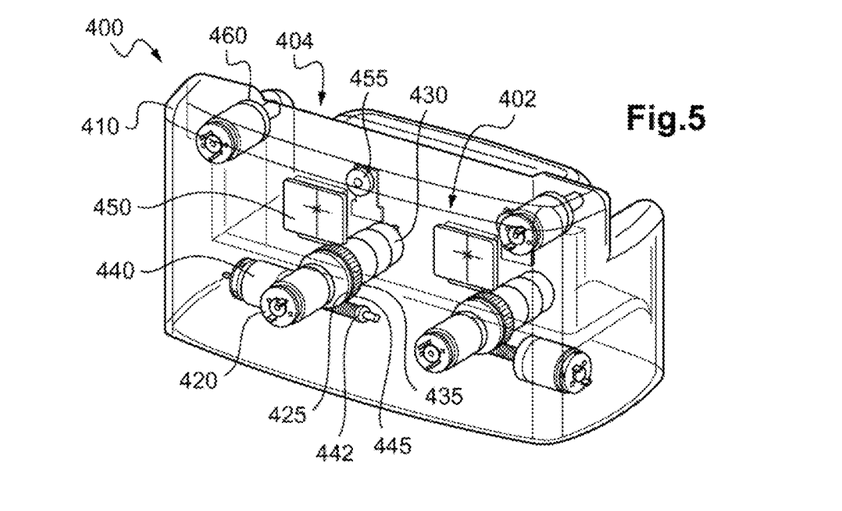
FIG. 5 represents an apparatus for receiving the spectacles of FIG. 4.

FIG. 5 represents a receiving apparatus 400 for the spectacles which have just been described.

Such a receiving apparatus 400 comprises a holder 410, here of parallelepipedal general shape, exhibiting a housing 402, open here at the top and dimensioned so as to accommodate the visual compensation spectacles 300, in particular the crosspiece 310, the support elements 315 and the optical assemblies 350.

The holder 410 also exhibits openings 404, formed in a lateral wall of the housing 402, for the passage of the temples 320 of the visual compensation spectacles 300.

For each optical assembly 350, the receiving apparatus 400 comprises:

a first (electric) motor for driving 420 a first transmission element 425 (here a toothed wheel placed on the output shaft of the first motor 420);

a second (electric) motor for driving 430 a second transmission element 435 (here a toothed wheel placed on the output shaft of the second motor 430);

a third (electric) motor for driving 440 a third transmission element 445 (here a toothed wheel driven by a screw 442 mounted on the output shaft of the third motor 440).

Figure 6:
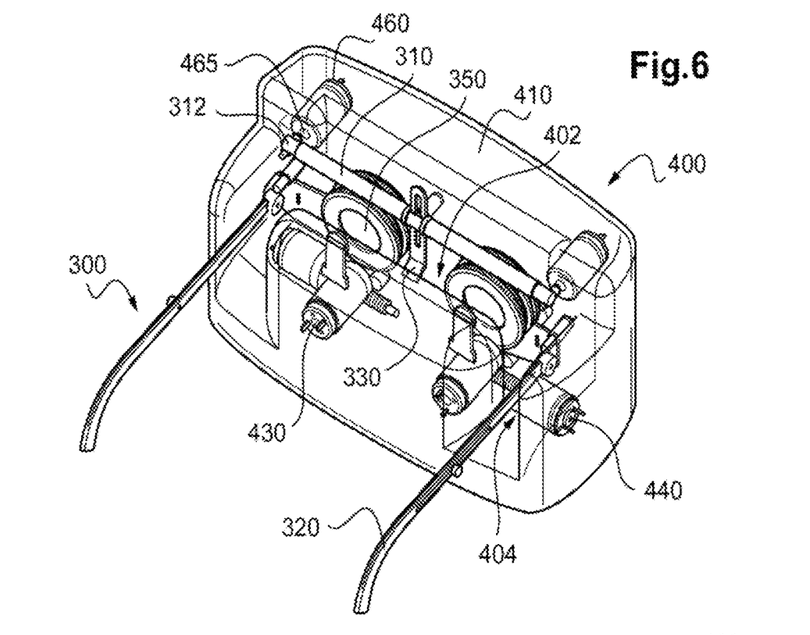
FIG. 6 represents the visual compensation spectacles of FIG. 4 received in the receiving apparatus of FIG. 5.

Each transmission element 425, 435, 445 is placed in the receiving apparatus (here in an opening of a back wall of the housing 402 formed in the holder 410) so as to cooperate with a control member 354, 356, 352 for the optical assembly 350 concerned when the visual compensation spectacles 300 are received in the receiving apparatus 400, as represented in FIG. 6.

Specifically, when the visual compensation spectacles 300 are received in the holder 410 (they being positioned in the housing 402, with the temples 320 passing through the openings 404):

the first transmission element 425 cooperates with the first control ring 354 (so that the first driving motor 420 and the first transmission element 425 form the first driving system mentioned above);

the second transmission element 435 cooperates with the second control ring 356 (so that the second driving motor 430 and the second transmission element 435 form the second driving system mentioned above);

the third transmission element 445 cooperates with the toothed wheel 352 (so that the third driving motor 440 and the third transmission element 445 form the third driving system mentioned above).

Thus, by action respectively of the first driving motor 420, of the second driving motor 430 and of the third driving motor 440, it is possible to adjust the cylindrical power, the spherical power and the axis of the cylindrical correction that are generated by the optical assembly 350 concerned.

In the example described here, the receiving apparatus 400 also comprises for each optical assembly 350 to be received in the housing 402, a system for checking the optical power comprising a display 450 and an imager (for example a camera 455) located respectively on either side of the housing 402 in a region intended to receive an optical assembly 350.

As also explained below, a control circuit 480 (here included in the receiving apparatus 400) is designed to determine the characteristics of the optical correction provided by the optical assembly 350 as a function of at least one image of the display 450 observed through the optical assembly 350 by the camera 455, by deflectometry calculation.

The receiving apparatus 400 comprises, finally, in association with each of the two sides of the frame of the visual compensation spectacles 300, a fourth (electric) motor for driving 460 a fourth transmission element 465.

This fourth transmission element 465 is positioned in the receiving apparatus 400 (that is to say in the holder 410) in such a way as to cooperate with a corresponding pinion 312 in such a way as to adjust (by action of the fourth driving motor 460) the position of the corresponding support element 315 in relation to the crosspiece 310.

Figures 7, 8:
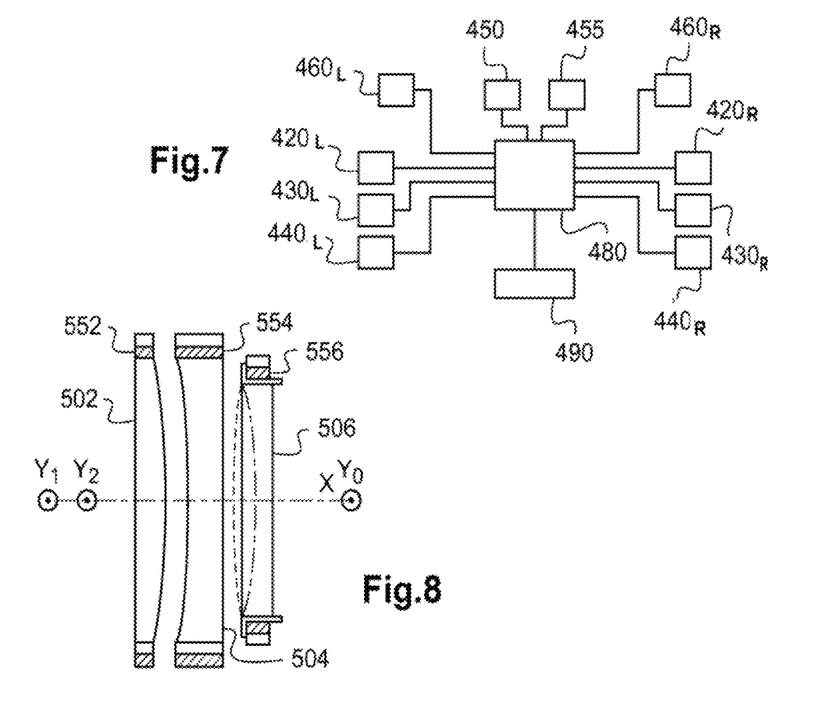
FIG. 7 schematically represents the main electronic components of the receiving apparatus of FIG. 5.
FIG. 8 represents a conceivable variant for the production of at least one optical assembly of the visual compensation spectacles of FIG. 4.

FIG. 7 schematically represents the main electronic components of the receiving apparatus 400.

The above-mentioned control circuit 480 comprises for example a processor (for example a microprocessor) and one or more memory (memories) which store, in particular, computer program instructions driving the implementation, by the control circuit 480, of the methods described hereinbelow when these instructions are executed by the processor.

Calibration data for the two modules 350 can furthermore be stored in one of the above-mentioned memories of the control circuit 480.

As a variant, the control circuit 480 could take the form of an application specific integrated circuit.

The receiving apparatus 400 also comprises a communication module 490, linked to the control circuit 480 and designed to establish a channel of communication with another electronic device (not represented), for example an auto-refractometer or a refractor.

The communication module 490 is for example designed to establish a wireless link with the other electronic device, here by connecting to a wireless local area network (or WLAN) to which the other electronic device is also connected. As a variant, the communication module 490 can establish a communication with the other electronic device via a wired link.

The control circuit 480 is also linked to the first driving motors $420_L$, $420_R$, to the second driving motors $430_L$, $430_R$, to the third driving motors $440_L$, $440_R$ and to the fourth driving motors $460_L$, $460_R$ (the driving motors intended to control the optical assembly associated with the left eye being referenced with the letter L as subscript, while the driving motors intended to control the optical assembly associated with the right eye are referenced with the letter R as subscript).

The control circuit 480 is finally linked to the display 450 and to the camera 455, as already indicated.

An exemplary use of the system which has just been described is now described.

The control circuit 480 receives setpoint information originating from the other electronic device, via the communication channel established by the communication module 490. This setpoint information comprises for example, for each eye, a spherical power setpoint S, a cylindrical power setpoint C, a cylindrical correction angle setpoint a and a semi-interpupillary distance setpoint PD.

These setpoints correspond for example to values (ametropia and physiological values in particular) measured on the wearer with the aid of the other electronic device (auto-refractometer or refractor).

It is considered that the visual compensation spectacles 300 are then placed in the receiving apparatus 400, as represented in FIG. 6.

The control circuit 480 then commands the fourth driving motors $460_L$, $460_R$ so as to place each of the optical assemblies 350 square with the corresponding optical power checking system (display 350, camera 355).

For each eye, the control circuit 480 thereafter commands the first driving motor 420, the second driving motor 430, the third driving motor 440 in such a way that the optical assembly 350 concerned generates an optical correction whose characteristics (spherical power, cylindrical power, axis of the cylinder) comply with the setpoint information received for the eye concerned.

In the example described here, the control circuit 480 determines at each instant the characteristics of the effective correction by means of the display 450 and of the camera 455 (by analysis of the images of the display 450 that are formed through the optical assembly 350 on the camera 455) and instructs the rotation of the driving motor 420, 430, 440 concerned until the setpoint value is obtained.

As a variant, the control circuit 480 can be designed to determine, by appropriate processing of the setpoint information received (using in particular the calibration data mentioned above), position setpoints for each of the control members 354, 356, 352 of the optical assembly 350, and to command the first driving motor 420, the second driving motor 430, the third driving motor 440 so as to attain these respective position setpoints.

In this case provision may be made for three frames of reference on each optical assembly 350 (respectively for the adjustment of spherical power, the adjustment of cylindrical power and the adjustment of the cylinder axis), which are identifiable by means of sensors securely fastened to the receiving apparatus 400, in such a way as to check the characteristics of the optical correction directly on the basis of the driving motors (due to the fact that the position of each control member 352, 354, 356 is known in its aforementioned frame of reference).

Once the desired correction has been obtained for each optical assembly 350, the control circuit 480 also commands (for each side) the fourth driving motor 460 in such a way as to set the position of the optical assembly 350 concerned to the semi-interpupillary distance PD desired (i.e. received as setpoint as indicated above).

The visual compensation spectacles 300 can then be removed from the receiving apparatus 400 and be used by the wearer, here to verify the validity of the measurements made at the level of the other electronic device.

FIG. 8 represents a conceivable variant for the production of at least one optical assembly of the visual compensation spectacles 300.

Such an optical assembly comprises:
a convex planar-cylindrical lens 502, of cylindrical power $C_0$ along the optical axis X, mounted on a first toothed wheel 552 rotatable about the optical axis X;
a concave planar-cylindrical lens 504, of negative cylindrical power $-C_0$ along the optical axis X, mounted on a second toothed wheel 554 rotatable about the optical axis X; and
a lens 506 of spherical power (along the optical axis) $S_V$ that can be varied by rotating a third toothed wheel 506 (the third toothed wheel 506 cooperating by a system of screw-nut type with an element for control of the radius of a membrane of the lens 506, as explained above for the lens 200).

The absolute value (or modulus), here $C_0$, of the cylindrical power (here $-C_0$) of the concave planar-cylindrical lens 504 is therefore equal to the absolute value ($C_0$) (or modulus) of the cylindrical power ($C_0$) of the convex planar-cylindrical lens 502.

Each of the three lenses 502, 504, 506 comprises a first planar face, perpendicular to the optical axis X, and a second face, opposite the first face and optically active:
the optically active face of the lens 502 is cylindrically convex in shape (the axis $Y_1$ of the cylinder defining this face lying perpendicular to the optical axis X);
the optically active face of the lens 504 is cylindrically concave in shape (the axis $Y_2$ of the cylinder defining this face lying perpendicular to the optical axis X); and
the optically active face of the lens 506 of variable spherical power $S_V$ is deformable and can thus take a convex spherical shape (as illustrated dashed in FIG. 8), a plane shape (as illustrated by a solid line in FIG. 8) or a concave spherical shape (as illustrated chain-dashed in FIG. 8).

The lens 506 of variable spherical power $S_V$ is for example a lens of the type described in document EP 2 034 338. Such a lens comprises a cavity closed by a transparent deformable membrane and a planar movable transparent wall;

the cavity contains a transparent liquid of constant volume that is constrained, to a greater or lesser degree, by the movable face, in order to deform the membrane that is thus either a spherical concave surface, or a planar surface, or a spherical convex surface. In the lens used, a transformation of motion achieved with a nut/bolt system makes it possible to ensure transformation of rotary and linear motion. Thus, a rotation of the toothed route 556 drives the above-mentioned control element in translation, thereby causing the deformation of the transparent membrane as explained for example in the aforementioned document EP 2 034 338. It is thus possible to vary the spherical power $S_V$ continuously via mechanical action on the lens 506. In the example described here, the lens 506 has a variable focal length of between $-40$ mm and 40 mm, i.e. a variable spherical power $S_V$ of between $-25D$ and 25D (D being the diopter, the unit for measuring vergence, inverse to the focal length expressed in meters).

Moreover, the planar-cylindrical lenses 502, 504 have respectively as already indicated a cylindrical power of $-C_0$ and $C_0$, here with $C_0=5D$.

By rotating the toothed wheel 552, the axis $Y_1$ of the convex cylinder formed on the optically active face of the convex planar-cylindrical lens 502 can form a variable angle $\alpha_1$ with a reference axis $Y_0$ (fixed and perpendicular to the optical axis X).

Likewise, by rotating the toothed wheel 554, the axis $Y_2$ of the concave cylinder formed on the optically active face of the concave planar-cylindrical lens 4 can form a variable angle $\alpha_2$ with the reference axis $Y_0$.

By calculating the vergence on the various meridians, the following formulae are obtained for the spherical power S, the cylindrical power C and the angle of astigmatism a of the system formed from the three optical elements 502, 504, 506 just described:

$$\tan 2\alpha = \frac{\sin 2\alpha_2 - \sin 2\alpha_1}{\cos 2\alpha_2 - \cos 2\alpha_1} = -\frac{\cos(\alpha_1 + \alpha_2)}{\sin(\alpha_1 + \alpha_2)} \quad \text{(formula 1)}$$

$$C = C_0(\cos 2(\alpha - \alpha_2) - \cos 2(\alpha - \alpha_1)) \quad \text{(formula 2)}$$

$$S = S_V - \frac{C}{2}. \quad \text{(formula 3)}$$

It is noted that the term ($-C/2$) in formula 3 corresponds to the spherical power generated by the resultant of the two cylindrical-power lenses 502, 504.

By virtue of its structure exhibiting three toothed wheels, such an optical assembly can easily cooperate (when it is mounted in visual compensation spectacles of the type represented in FIG. 4) with a receiving apparatus 400 such as described above.

By controlling the rotational position of the convex planar-cylindrical lens 502 (by means of the first driving motor 420) and the rotational position of the concave planar-cylindrical lens 504 (by means of the third driving motor 440), independently of one another, as described hereinafter, it is possible to independently vary each of the angles $\alpha_1$, $\alpha_2$ from $0°$ to $360°$ and thus obtain a cylindrical power C adjustable between $-2.C_0$ and $2.C_0$ (i.e. here between $-10D$ and $10D$), and to do so for any angle of astigmatism adjustable between $0°$ and $360°$ obtained by simultaneous control of the two lenses. As indicated by formula number 3, the resultant of spherical power induced by the resultant of the orientation of the two cylindrical lenses 502, 504 is compensated for with the aid of the variable power spherical lens 506.

In this context provision may also be made for a mechanism of synchronization between the two cylindrical lenses 502, 504 in such a way that the latter rotate in opposite senses by an identical angle.

Moreover, by varying the spherical power $S_V$ of the spherical lens 6 (with the aid of the second driving motor 430), it is possible to adjust the spherical power S of the system formed of the three lenses 502, 504, 506.

The invention claimed is:

1. An optometry apparatus comprising:
   a holder configured to receive visual compensation spectacles, the holder including an open housing dimensioned to accommodate the visual compensation spectacles, and openings formed in a wall of the open housing and configured for the passage of temples of the visual compensation spectacles;
   at least one transmission element configured to cooperate with a member to adjust an optical correction characteristic of said spectacles; and
   at least one motor configured to drive the transmission element.

2. The optometry apparatus as claimed in claim 1, further comprising
   a communication module configured to receive a setpoint originating from an exterior electronic device; and
   a control module configured to control the driving motor as a function of the received setpoint.

3. A system comprising:
   the optometry apparatus as claimed in claim 2; and
   said exterior electronic device that is another optometry device.

4. The system as claimed in claim 3, wherein the other optometry device is an auto-refractometer or a refractor.

5. The system as claimed in claim 4, wherein said exterior electronic device determines said setpoint as a function of an ametropia or astigmatism measurement.

6. The system as claimed in claim 3, wherein said exterior electronic device determines said setpoint as a function of an ametropia or astigmatism measurement.

7. The optometry apparatus as claimed in claim 2, further comprising:
   a display and an imager which are disposed on either side of a region of reception of the visual compensation spectacles.

8. The optometry apparatus as claimed in claim 1, further comprising:
   a display and an imager which are disposed on either side of a region of reception of the visual compensation spectacles.

9. The optometry apparatus as claimed in claim 8, further comprising:
   a module for analysis of an image of the display, generated by the imager; and
   a module for control of the driving motor as a function of data generated by the analysis module.

10. An assembly comprising:
    an optometry apparatus; and
    visual compensation spectacles,
    the optometry apparatus comprising
      a holder configured to receive said spectacles, the holder including an open housing dimensioned to accommodate the visual compensation spectacles, and openings formed in a wall of the open housing and configured for the passage of temples of the visual compensation spectacles,
      at least one transmission element configured to cooperate with a member to adjust an optical correction characteristic of said spectacles, and
      at least one motor configured to drive the transmission element.

11. The assembly as claimed in claim 10, wherein the visual compensation spectacles comprise at least one lens having an optical axis and are configured to modify, in case of movement of the adjusting member, a spherical power along the optical axis, generated by said lens.

12. The assembly as claimed in claim 10, wherein the visual compensation spectacles comprise at least one lens having an optical axis and are configured to modify, in case of movement of the adjusting member, a cylindrical correction along the optical axis, generated by said lens.

13. The assembly as claimed in claim 12, wherein the visual compensation spectacles are configured to modify, in case of movement of the adjusting member, a power of said cylindrical correction.

14. The assembly as claimed in claim 12, wherein the visual compensation spectacles are to modify, in case of movement of the adjusting member, an axis of said cylindrical correction.

* * * * *